(12) United States Patent
DiVenuta et al.

(10) Patent No.: US 7,558,380 B2
(45) Date of Patent: Jul. 7, 2009

(54) METHODS, SYSTEMS AND COMPUTER PROGRAM PRODUCTS FOR PROVIDING TARGETED MESSAGES FOR PHARMACY INTERACTIVE VOICE RESPONSE (IVR) SYSTEMS

(75) Inventors: Dennis M. DiVenuta, Raleigh, NC (US); Frank Sheppard, Raleigh, NC (US); Jeffrey L. Slater, Raleigh, NC (US)

(73) Assignee: ATEB, Inc., Raleigh, NC (US)

( * ) Notice: Subject to any disclaimer, the term of this patent is extended or adjusted under 35 U.S.C. 154(b) by 1167 days.

(21) Appl. No.: 10/672,556

(22) Filed: Sep. 25, 2003

(65) Prior Publication Data

US 2005/0069103 A1    Mar. 31, 2005

(51) Int. Cl.
*H04M 11/06* (2006.01)

(52) U.S. Cl. .............. 379/88.18; 235/375; 235/385; 235/462.01; 379/88.22; 705/2; 705/3

(58) Field of Classification Search .............. 379/88.18, 379/88.22; 705/2, 3; 235/385, 375, 462.01
See application file for complete search history.

(56) References Cited

U.S. PATENT DOCUMENTS

| | | | | |
|---|---|---|---|---|
| 4,766,542 A | * | 8/1988 | Pilarczyk ................... 705/3 |
| 5,612,869 A | * | 3/1997 | Letzt et al. ................. 705/3 |
| 5,970,124 A | | 10/1999 | Csaszar et al. |
| 5,996,006 A | | 11/1999 | Speicher |
| 6,055,513 A | | 4/2000 | Katz et al. |
| 6,202,923 B1 | * | 3/2001 | Boyer et al. ............... 235/375 |
| 6,298,330 B1 | | 10/2001 | Gardenswartz et al. |
| 6,578,003 B1 | * | 6/2003 | Camarda et al. ............... 705/3 |
| 6,680,999 B1 | * | 1/2004 | Garcia ..................... 379/88.22 |
| 7,058,584 B2 | * | 6/2006 | Kosinski et al. ................. 705/2 |
| 7,267,278 B2 | * | 9/2007 | Lammle ................ 235/462.01 |
| 2002/0010584 A1 | | 1/2002 | Schultz et al. |
| 2002/0052760 A1 | * | 5/2002 | Munoz et al. .................. 705/2 |
| 2002/0164004 A1 | | 11/2002 | Tamura et al. |
| 2006/0149587 A1 | * | 7/2006 | Hill et al. ...................... 705/2 |
| 2007/0119930 A1 | * | 5/2007 | Jordan et al. ................ 235/385 |

OTHER PUBLICATIONS

Letter from Michael R. Friscia to Mitchell S. Bigel dated Jun. 27, 2006.

Press release dated Jan. 9, 2001 by Harland Financial Solutions, entitled "Harland Financial Solutions and Maxxar Corporation Establish Alliance to Bring One-to-One Marketing to Telephone Banking", 2 pp., downloaded Apr. 13, 2006 from http://www.harlandfinancialsolutions.com/NewsandEvents/PrintRelease.asp?id=104.

(Continued)

*Primary Examiner*—Gerald Gauthier
(74) *Attorney, Agent, or Firm*—Myers Bigel Sibley & Sajovec

(57) ABSTRACT

A pharmacy Interactive Voice Response (IVR) system can identify a targeted message for playing to a caller using criteria that are based on a prescription number that is provided by the caller. The functionality of an IVR system can thereby be enhanced to provide targeted educational messages concerning the pharmaceutical prescription, targeted messages that indicate alternative medications that may substituted for the pharmaceutical prescription, targeted messages that identify other items that may be desired, targeted messages that solicit participation in a study related to the pharmaceutical prescription and/or other targeted messages. Related systems and computer program products are also discussed.

41 Claims, 11 Drawing Sheets

OTHER PUBLICATIONS

Brochure dated Sep. 2003 by CTG, entitled "Customer Capture—CTG Implements a Customer-Specific Marketing Program for a Major Retailer", 2 pp.

Brochure dated Mar. 2006, entitled "TeleVoice—The next Generation of Voice Response for Mortgage Servicing Call Centers", 6 pp.

Website printout dated Apr. 13, 2006 by Covansys, entitled "Case Studies—Client: State of Michigan Office of Retirement Services", 4 pp, downloaded Apr. 13, 2006 from http://www.covansys.com/clients/case_michigan.htm.

* cited by examiner

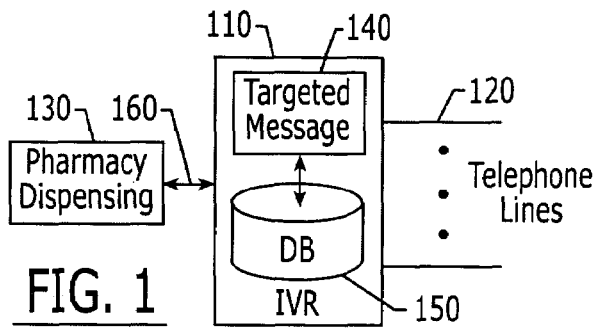
FIG. 1
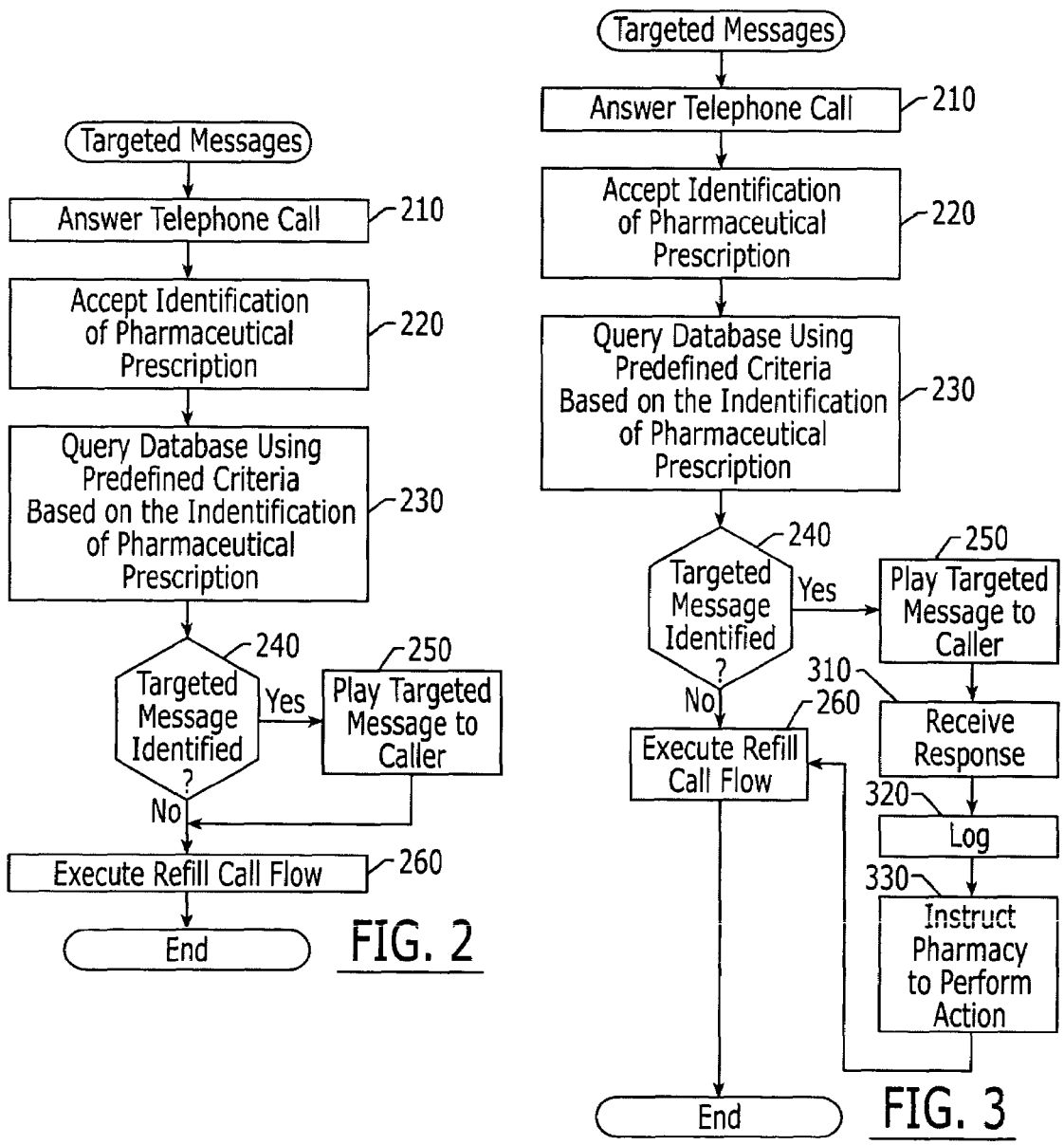
FIG. 2
FIG. 3

METHODS, SYSTEMS AND COMPUTER PROGRAM PRODUCTS FOR PROVIDING TARGETED MESSAGES FOR PHARMACY INTERACTIVE VOICE RESPONSE (IVR) SYSTEMS

FIELD OF THE INVENTION

This invention relates to Interactive Voice Response (IVR) systems, and more specifically to IVR systems that are used in pharmacies.

BACKGROUND OF THE INVENTION

IVR systems are widely used to disseminate and provide information to telephone callers through automated sequences of voice prompts and menu options. IVR systems can allow callers to perform various transactions without the need for direct assistance from a customer service representative or associate. IVR systems are well known to those having skill in the art and need not be described further herein. IVR systems also may be referred to in the art as Voice Response Units (VRU) and/or other designations, which are encompassed herein by the term IVR.

One widely used application of IVR systems is in a pharmacy. These systems, also referred to herein as pharmacy IVR systems, may be used in a standalone pharmacy and/or a pharmacy department of a larger establishment. A pharmacy IVR system can allow callers to access the pharmacy services by telephone when the pharmacy is open and/or when the pharmacy is closed. The pharmacy IVR system can automatically handle telephone calls into the pharmacy. Pharmacy customers and doctors may thereby benefit, because they can enter pharmaceutical prescription refills into the IVR system at their convenience, during and/or outside of business hours and without the need to wait on hold.

As is well known to those having skill in the art, a pharmacy IVR system can operate on a standalone computer, can be installed on the same computer that runs a pharmacy dispensing and/or management system and/or can be installed on a computer that provides other general functions. The pharmacy IVR system can automatically answer telephone calls to the pharmacy and can integrate with the pharmacy dispensing system database. A pharmacy IVR system can accept prescription refill requests from customers, accept messages from customers, update the pharmacy dispensing system with valid customer refill requests, record voice messages from doctors for new prescriptions and refill authorizations, record general messages from doctors, announce pharmacy hours to callers, transfer calls to a pharmacist, automatically transmit messages to doctors for refill authorization, allow callers to check on the status of their prescription refill request(s) and/or perform other functions.

SUMMARY OF THE INVENTION

Some embodiments of the present invention operate a pharmacy Interactive Voice Response (IVR) system in response to a telephone call by a caller to the pharmacy IVR system, by identifying a targeted message for playing to the caller, using predefined criteria that are based on an identification of a pharmaceutical prescription by the caller. Accordingly, embodiments of the invention can allow an IVR system to deliver targeted messages to callers based on predefined criteria that are based on an identification of a pharmaceutical prescription by the caller. The functionality of a conventional IVR system can be enhanced to provide targeted educational (including promotional) messages concerning the pharmaceutical prescription, targeted messages that indicate alternative medications that may be substituted for the pharmaceutical prescription, targeted messages that identify other items such as medications or supplies that may be desired, targeted messages that solicit participation in a study related to the pharmaceutical prescription and/or other targeted messages, based on the specific pharmaceutical prescription that is identified by the caller and is being used by the caller or a party related to the caller for whom the caller has called.

In some embodiments of the present invention, a pharmacy IVR system answers a telephone call from a caller and accepts identification of a pharmaceutical prescription (e.g., prescription number) from a caller. At least one database is queried using predefined criteria based on the identification of a pharmaceutical prescription, to identify a targeted message. The targeted message is played to the caller. In some embodiments, after playing the targeted message, a refill call flow for the pharmaceutical prescription is executed (i.e., a refill call flow is begun or continued). In other embodiments, a series of targeted messages may be provided. In still other embodiments, a caller response to the targeted message is received and, in still other embodiments, the caller response and/or other events are logged. In still further embodiments, the pharmacy is instructed to perform an action in response to the caller response to the targeted message(s).

In some embodiments, the querying is performed by querying at least one pharmacy dispensing system database using the identification of the pharmaceutical prescription to identify the predetermined criteria. At least one message database is then queried using the predetermined criteria to identify a targeted message(s).

In some embodiments of the present invention, the predefined criteria based on the identification of a pharmaceutical prescription include age of a patient, a gender of the patient, medication of the pharmaceutical prescription, last fill date of the pharmaceutical prescription, days supply on last fill of the pharmaceutical prescription, original fill date of the pharmaceutical prescription, disease state of the patient, physician of the patient and/or other promotions that are in effect. In some embodiments, the predefined criteria do not include a personal identification of the patient, for privacy and/or other reasons. It will be understood that, as used herein, "patient" refers to the user of the pharmaceutical prescription, who may be the caller in some circumstances, but who also may be a parent, child, relative or friend of the caller in other circumstances.

In some embodiments, the querying is performed by querying at least one database using one or more of the above-described predefined criteria. A targeted message is identified that corresponds to the age of the patient, gender of the patient, medication of the pharmaceutical prescription, last fill date of the pharmaceutical prescription, days supply on last fill of the pharmaceutical prescription, original fill date of the pharmaceutical prescription, disease state of the patient, physician of the patient and/or other promotions in effect. If more than one targeted message satisfies the predefined criteria, the messages may be prioritized in some embodiments.

In some embodiments, at least one database is queried using the predefined criteria based on the identification of the pharmaceutical prescription, to identify an educational (informational) targeted message related to the pharmaceutical prescription. For example, at least one database is queried to determine whether days supply on last fill date exceeds a threshold and an educational targeted message may be provided that reminds the caller how to use the pharmaceutical prescription if the days supply on last fill date exceeds the threshold.

In other embodiments, if the last fill date is less than a first threshold and the days supply on last fill date exceed a second threshold, then a targeted message may be provided that indicates alternative medications that may be substituted for the pharmaceutical prescription. In still other embodiments, if the last fill date is less than a first threshold and the days supply on last fill date exceed a second threshold, then a targeted message may be provided that indicates other items, such as related medications or supplies, that may be desired by the patient. In these embodiments, the first threshold may be equal or unequal to the second threshold. Finally, in still other embodiments, a determination is made as to whether the age of the patient qualifies the patient to participate in a study related to the pharmaceutical prescription, and a targeted message is provided that solicits participation of the patient in the study, if the age of the patient qualifies the caller to participate. The study can include any type of conventional study or surveys including post-market surveys and medication use surveys.

It will be understood that although the above description has focused primarily on method aspects, other embodiments of the present invention may provide pharmacy IVR systems, systems for operating a pharmacy IVR system and/or computer program products for operating a pharmacy IVR system. Moreover, other embodiments of the present invention may be employed in a non-pharmacy environment, wherein targeted messages may be provided based on an identification other than a pharmaceutical prescription, such as an employee number, a Social Security number or an insurance identification number, using predefined criteria based on the user input to identify a targeted message.

BRIEF DESCRIPTION OF THE DRAWINGS

FIG. 1 is a block diagram of systems, methods and/or computer program products for providing targeted messages in a pharmacy IVR system according to some embodiments of the present invention.

FIGS. 2 and 3 are flowcharts of operations that may be performed to provide targeted messages according to some embodiments of the present invention.

DETAILED DESCRIPTION

Figure 4A:
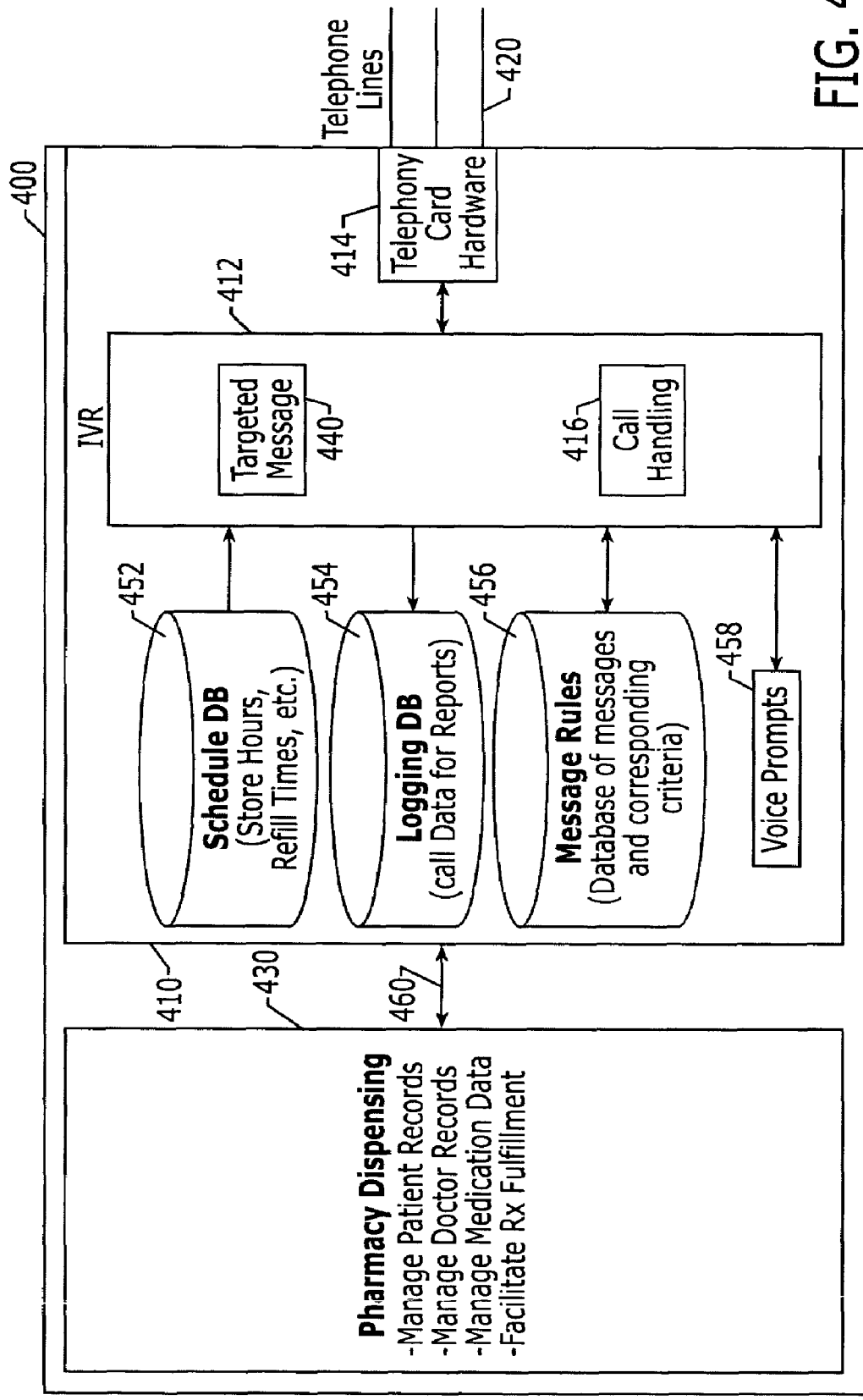
FIGS. 4A and 4B are block diagrams of systems, methods and/or computer program products for providing targeted messages in a pharmacy IVR system according to other embodiments of the present invention.

The present invention now will be described more fully hereinafter with reference to the accompanying figures, in which embodiments of the invention are shown. This invention may, however, be embodied in many alternate forms and should not be construed as limited to the embodiments set forth herein.

Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention as defined by the claims. Like numbers refer to like elements throughout the description of the figures.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

FIG. 1 is a block diagram of systems, methods and/or computer program products for providing targeted messages in a pharmacy IVR system according to some embodiments of the present invention. As shown in FIG. 1, an IVR system 110 is coupled to one or more telephone lines 120 to receive telephone calls from callers. The IVR system can include prerecorded voice prompts such as prerecorded human voice segments, stored text-to-speech generated segments, text-to-speech segments that are generated on the fly, and/or use other conventional techniques for generating voice prompts. The IVR system 110 also is coupled to a pharmacy dispensing system 130, also referred to as a pharmacy management system, which may be used to manage patient records, manage doctor records, manage medication data, facilitate prescription fulfillment and/or perform other pharmacy management functions. Conventional pharmacy IVR systems 110 and pharmacy dispensing systems 130 as described in this paragraph are well known to those having skill in the art and need not be described further herein. Moreover, it will be understood that the IVR system 110 and the pharmacy dispensing system 130 may be combined to run on a single enterprise, application or personal computer system. Alternatively, the IVR system 110 and/or the pharmacy dispensing system 130 may be distributed over more than one enterprise, application, personal and/or pervasive computer systems, which may be connected by a network 160 such as a local area network and/or a wide area network including the Internet.

Still referring to FIG. 1, a targeted message module 140 is provided according to some embodiments of the present invention. The targeted message module 140 may comprise hardware and/or software. The targeted message module 140 is configured to identify a targeted message for playing to a caller over telephone lines 120 using predefined criteria that are based on an identification of a pharmaceutical prescription by the caller. The predefined criteria for identifying a targeted message may be stored in at least one database 150 as will be described in detail below. It will be understood by those having skill in the art that the targeted message module 140 and/or database 150 may be integrated within the IVR system 110 in some embodiments. In other embodiments, the targeted message module 140 and/or database 150 may be provided, at least in part, separate from the IVR system 110 on one or more enterprise, application, personal and/or pervasive computer systems that may be connected to the IVR system using a network such as a local area network and/or a wide area network including the Internet.

Targeted message systems, methods and/or computer program products according to embodiments of the present invention can provide the pharmacy and/or other interested parties an ability to provide targeted informational messages, targeted promotional messages, targeted surveys and/or other targeted messages to callers refilling prescriptions. In some embodiments, the pharmacy IVR system may be operated in response to a telephone call by a caller to the pharmacy IVR system, by identifying a targeted message for playing to the caller using predefined criteria that are based on identification of the pharmaceutical prescription by the caller. In some embodiments, the pharmacy IVR system may have access to specific patient data through the pharmacy dispensing system 130, based on the identification of the pharmaceutical prescription by the caller. Using this data, the targeted message module 140 may retrieve various predefined identifiers that indicate callers as candidates to hear a specific targeted message that may directly relate to their prescription. If a patient meets a set of identified criteria that matches a targeted message, the targeted message module 140 can play the message(s) to the caller and gather any responses through the IVR system 110. It will be understood by those having skill in the art that a message can include a single voice message, a series of voice messages, or a complex message flow. It also will be understood that standard IVR techniques may be used to store, retrieve, update and/or delete messages by the targeted message module.

FIG. 2 is a flowchart of operations that may be performed to provide targeted messages according to some embodiments of the present invention. These operations may be provided, for example, by the targeted message module 140 of FIG. 1, using the IVR system 110 and/or the pharmacy dispensing system 130.

Referring now to FIG. 2, at Block 210, a telephone call from a caller is answered. It will be understood that the caller may be the patient (i.e., the user of the medication of the pharmaceutical prescription) or a caller who is calling on behalf of the patient, such as a relative or friend of the patient.

In some embodiments, upon a caller's initial contact, the caller may select whether or not to participate in the targeted messages and may also select the level of targeted messages the caller wishes to hear. For example, callers may be provided an option to automatically hear informational or educational messages, such as compliance data (for example, "Be sure to take food with your medication"). The caller may choose to hear promotions and advertising related to the caller's specific medications. Alternatively, callers may opt out of all targeted messages completely. In other embodiments, only some or none of these caller options may be provided.

Still referring to FIG. 2, at Block 220, an identification of a pharmaceutical prescription may be obtained from the caller. The identification of a pharmaceutical prescription generally is a prescription number ("Rx number"), which may be entered by the caller using the telephone keypad and/or speech recognition. At Block 230, at least one database, such as a database 150 of FIG. 1 and/or a database in the pharmacy dispensing system 130, is queried using predefined criteria based on the identification of a pharmaceutical prescription, to identify a targeted message. In some embodiments, the predefined criteria based on identification of a pharmaceutical prescription can comprise age of the patient, gender of the patient, medication of the pharmaceutical prescription, last fill date of the pharmaceutical prescription, days supply on last fill of the pharmaceutical prescription, original fill date of the pharmaceutical prescription, disease state of the patient, physician of the patient and/or other promotions in effect. In other embodiments, the predefined criteria based on identification of a pharmaceutical prescription do not provide a personal identification of the patient for privacy or other reasons. In some embodiments, at least one pharmacy dispensing system database, such as at least one database in the pharmacy dispensing system 130, is queried using the identification of the pharmaceutical prescription to identify the predetermined criteria. Then, at least one message database, such as at least one database 150 that is associated with the targeted message module 140, is queried using the predetermined criteria to identify a targeted message.

Still referring to FIG. 2, at Block 240, if a targeted message is identified, then the targeted message is played to the caller, at Block 250. More specifically, in some embodiments, at Block 240, a targeted message that corresponds the age of the patient, gender of the patient, medication of the pharmaceutical prescription, last fill date of the pharmaceutical prescription, days supply on last fill of the pharmaceutical prescription, original fill date of the pharmaceutical prescription, disease state of the patient, physician of the patient and/or other promotions in effect, is identified based on the database query. In some embodiments, the targeted message may comprise an educational message concerning the pharmaceutical prescription, a message that indicates alternative medications that may be substituted for the pharmaceutical prescription, a message that identifies other items (related and/or unrelated to the pharmaceutical prescription) that may be desired by the patient and/or a message that solicits participation of the patient in a study related to the pharmaceutical prescription. It will be understood that, in some embodiments, the targeted message need not be played to the caller during the same telephone call. Rather, in some embodiments, the call can be terminated, and a targeted message may be played at a later time, to the original caller and/or to the patient, in a new call that may be originated by the IVR system.

Examples of criteria, targeted messages and their generation according to some embodiments of the present invention, will be described in detail below. However, it will be understood by those having skill in the art that these examples of criteria and targeted messages are only exemplary and many other criteria and/or targeted messages may be generated and used according to other embodiments of the present invention. Finally, at Block 260, if a targeted message is not identified at Block 240, or after playing the targeted message at Block 250, a refill call flow may be executed (i.e., begun or continued) in some embodiments of the present invention at Block 260, for example to continue the refill call flow for the pharmaceutical prescription for which the caller initially placed the telephone call.

FIG. 3 illustrates operations that may be performed according to other embodiments of the present invention. In FIG. 3, the operations of Blocks 210, 220, 230, 240 and 250 are performed. At Block 310, a response is received from the caller to the targeted message. At Block 320, the caller response to the targeted message may be logged. It also will be understood that other caller responses and/or other events may be logged, as will be described below. Moreover, at Block 330, in some embodiments, the pharmacy is instructed to perform an action in response to the caller response to the targeted message. For example, the pharmacy may be instructed, for example, via the pharmacy dispensing system 130, to dispense an alternative medication, another item and/or study-related materials based on the response of the caller to the targeted message.

Figure 4B:
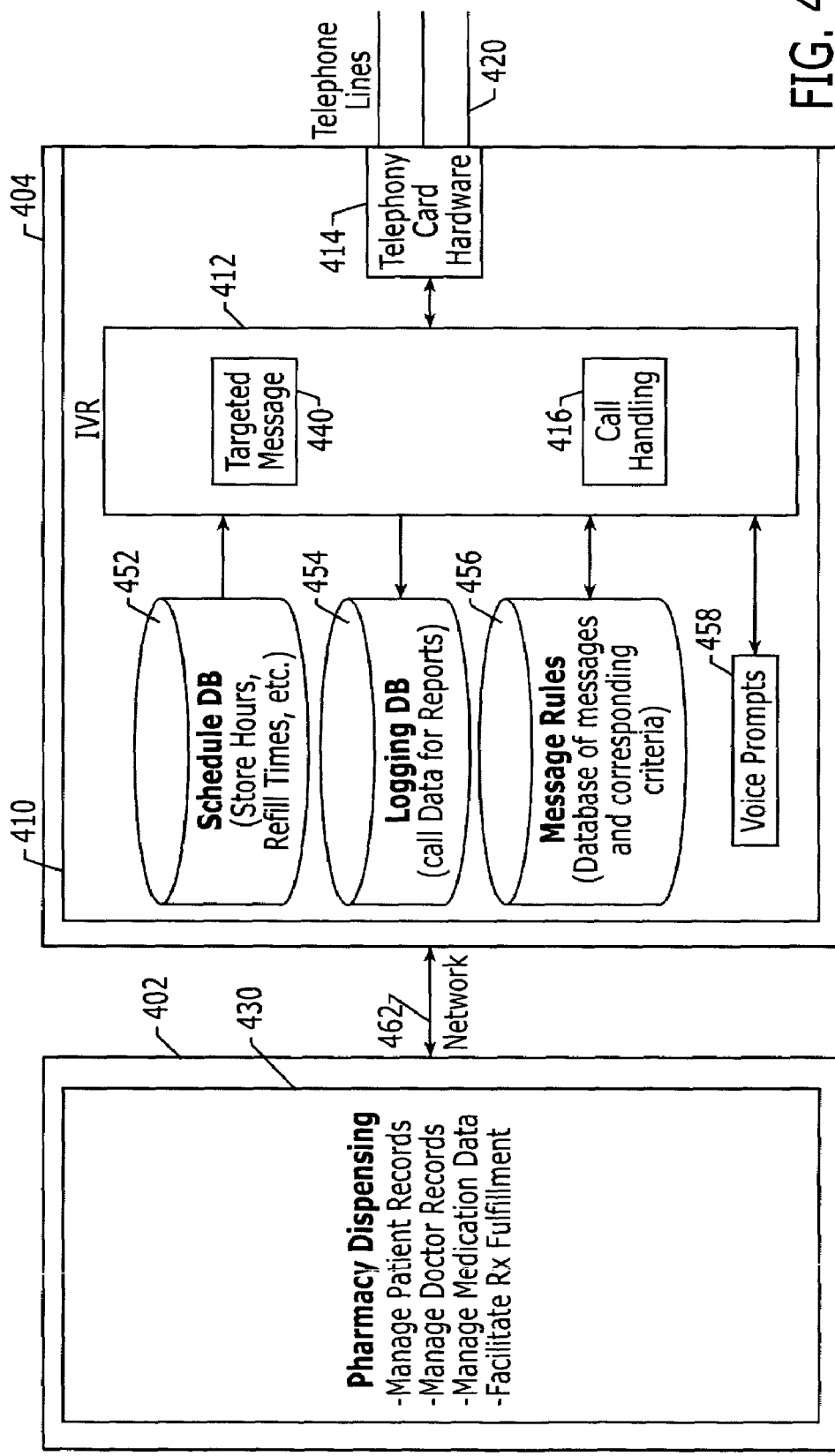

FIGS. 4A and 4B are detailed block diagrams of systems, methods and/or computer program products for providing targeted messages in a pharmacy IVR system according to other embodiments of the present invention. In FIG. 4A, the pharmacy dispensing system 430 and the IVR system 410 are both included in a single data processing system 400, which may include one or more enterprise, application, personal and/or pervasive computer systems. The IVR system 410 and the pharmacy dispensing system 430 may be connected by an internal hardware and/or software interface 460. In contrast, in FIG. 4B, the pharmacy dispensing system 430 is contained in a first data processing system 402, and the IVR system 410 is contained in a second data processing system 404 that are connected by a network 462, which may include a local and/or wide area network including the Internet. Each of the first and second data processing systems 402 and 404, respectively, may include one or more enterprise, application, personal and/or pervasive computer systems.

Still referring to FIGS. 4A and 4B, the pharmacy dispensing system 430 can include functionality for managing patient records, managing doctor records, managing medication data and/or facilitating prescription (Rx) fulfillment. The IVR system 410 may include telephony card hardware 414 for managing telephone lines 420, and a hardware and/or software controller 412 that includes a call handling module 416 and/or other conventional IVR modules. A targeted message module 440, which may correspond to the targeted message module 140 of FIG. 1, also may be included.

A plurality of databases are shown in FIGS. 4A and 4B. In particular, a schedule database 452 may be employed to store therein the pharmacy hours, refill times and/or other scheduling data. A logging database 454 may log call data and/or other events for reports. A message rules database 456 can store therein messages and corresponding criteria that can trigger a message. Finally, a voice prompts database 458 can store therein the voice prompts that are used. It will be understood that some or all of the functionality of databases 452-458 may be combined into one or more databases, which may correspond, for example, to the database 150 of FIG. 1. Accordingly, as used herein, a database includes a centralized or distributed database.

Figure 5:
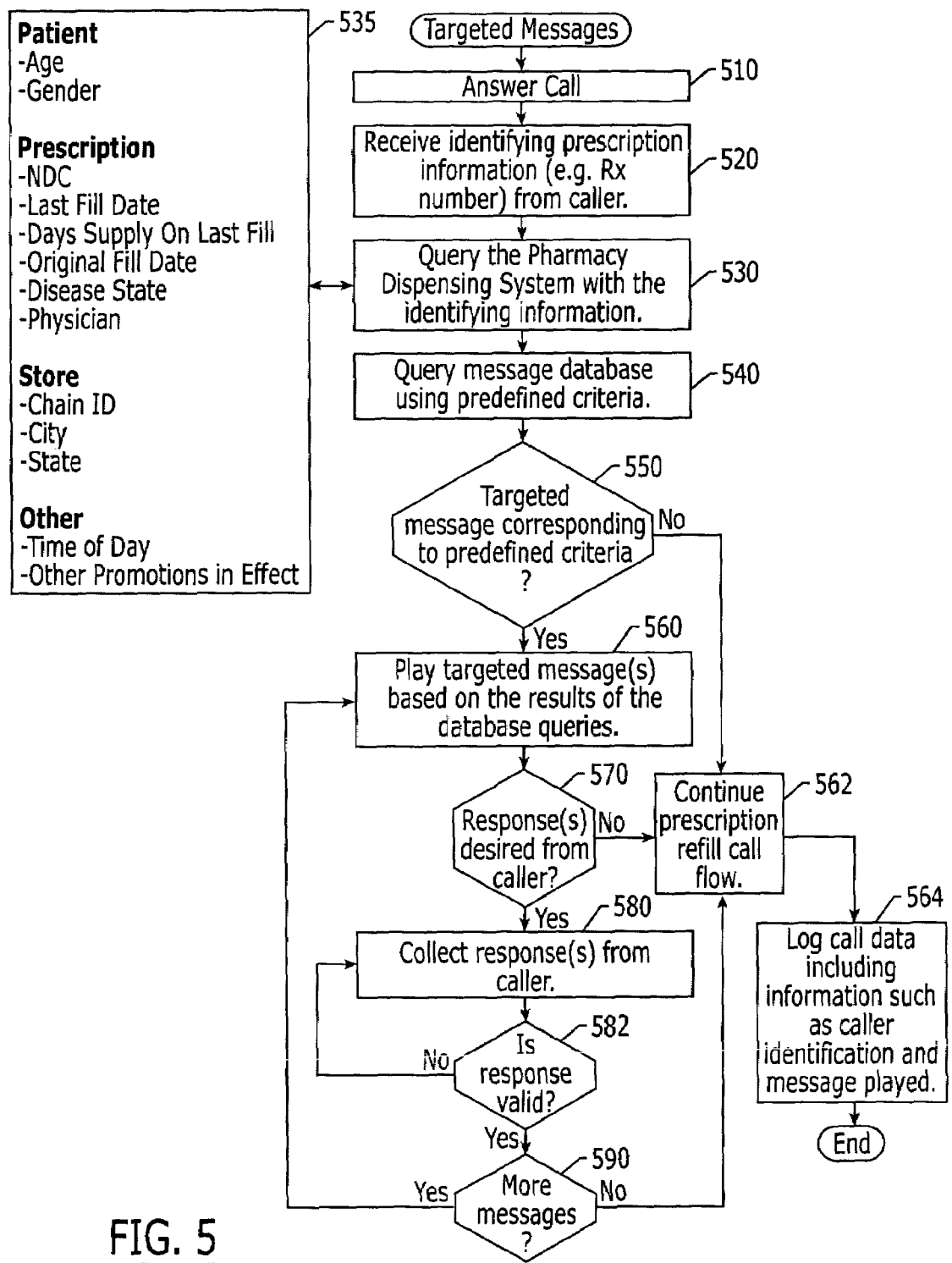
FIG. 5 is a flowchart of operations that may be performed to provide targeted messages according to some embodiments of the present invention.

FIG. 5 is a flowchart of operations that may be performed to provide targeted messages according to some embodiments of the present invention. In particular, referring to FIG. 5, at Block 510, the pharmacy IVR system answers calls from a caller. At Block 520, once a caller indicates that the caller would like to refill a prescription, the IVR prompts the caller to enter the prescription number or other identification of a pharmaceutical prescription at Block 520. Then, at Block 530, the pharmacy dispensing system is queried with the identifying information (e.g., pharmaceutical prescription number). As shown at Block 535, the pharmacy dispensing system and/or IVR system may include one or more patient databases that may include patient age and patient gender. One or more prescription databases may also include information about the pharmaceutical prescription, such as the National Drug Code (NDC) (i.e., the medication of the pharmaceutical prescription), last fill date, days supply on last fill, original fill date, disease state and physician. One or more store databases may also include information on the pharmacy itself, such as a chain ID, city and state. Other databases may include time of day and other promotions that are in effect. It will be understood that combinations and subcombinations of these databases may be merged into one or more databases. At Block 530, the IVR uses the prescription number or other entered information to identify predetermined criteria related to the patient or the patient's medication. It will be understood that, in some embodiments, the actual identity of the patient need not be provided, but only information concerning the patient/medication may be identified.

Then, at Block 540, the information that was obtained is compared with a message database, such as a message rules database 456 of FIGS. 4A and 4B, in order to determine which targeted messages may be pertinent and which messages to play. At Block 550, if a targeted message corresponds to, e.g., matches, the predefined criteria based on the prescription number, then at Block 560, targeted messages are played based on the results of the database queries. This message is targeted in that it can directly address specific needs or conditions of the caller.

If a targeted message corresponding to the predefined criteria is not found at Block 550, then the prescription refill call flow may be continued at Block 562, to process the caller's original prescription refill request. At Block 564, the IVR may log all call data and/or selected call data. Logging may be performed for reporting and/or call analysis. Logging data may include identification of the caller, messages played, date and time of call, caller responses including DTMF tones, length of call, hang-ups for non-completed messages, message interruptions by caller responses, etc.

Returning to Block 550, if a targeted message is identified at Block 550, the targeted messages are played based on the results of the database queries, at Block 560. If a response is desired from the caller, at Block 570, then one or more responses are collected from the caller at Block 580, with standard or other tests being made at Block 582 to validate responses. A response may be desired at Block 570, for example, if the caller is given the option to switch to a different medication or is offered the opportunity to complete a customer survey. A response may be checked for validity at Block 582 by verifying the proper number of characters and/or performing other validation tests.

Finally, at Block 590, if more messages are available, the caller is returned to the message portion of the call flow (Block 560). If the messages and/or customer action is complete, at Block 590, the IVR continues the call flow at Block 562, to process the refill request. It thus will be understood that a single targeted message, a series of related targeted messages or a plurality of unrelated targeted messages may be provided according to various embodiments of the invention.

Figure 6:
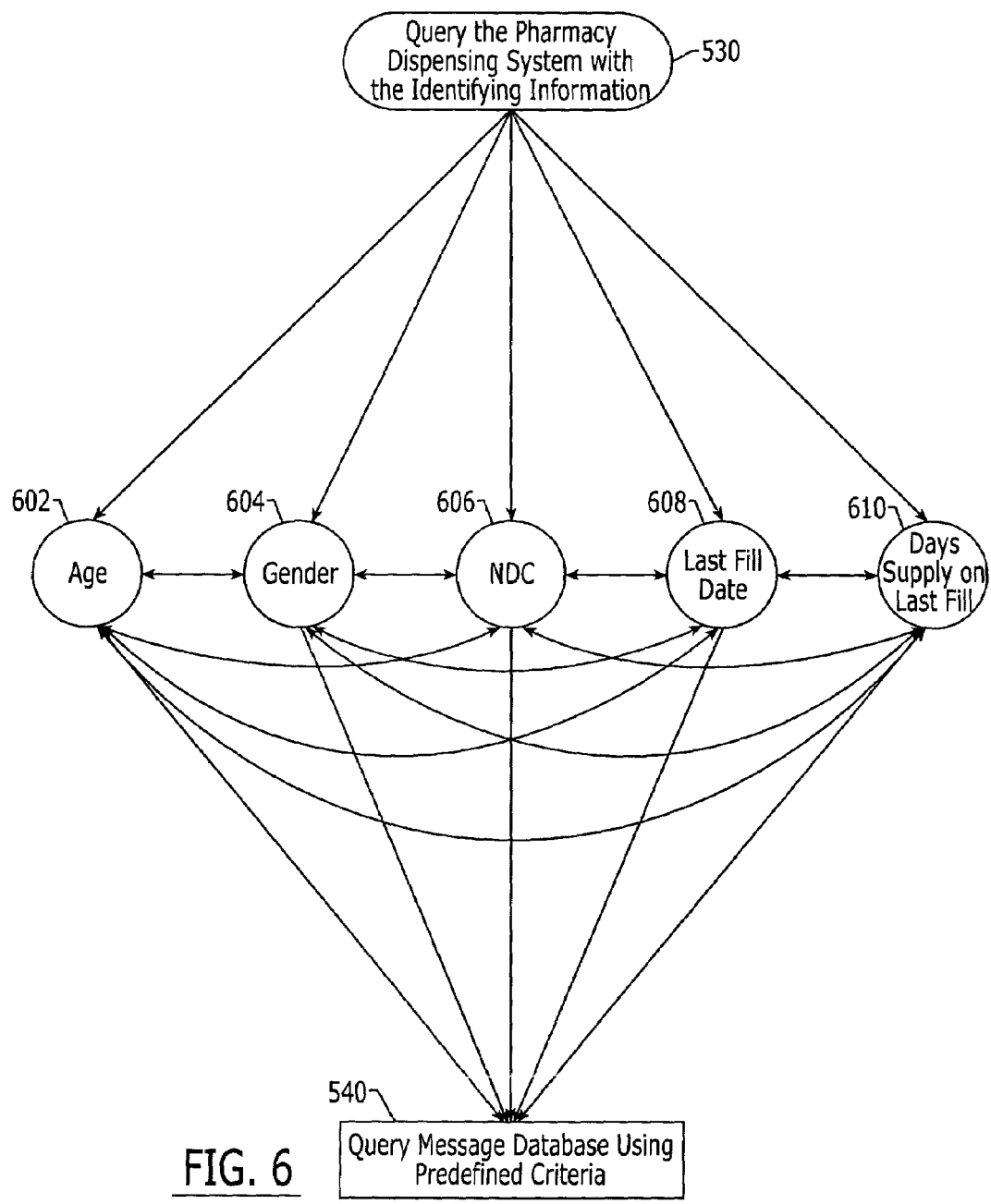
FIGS. 6 and 7 are flowcharts that illustrate various combinations of predetermined criteria that may be used to identify targeted messages according to various embodiments of the present invention.
Figure 7:
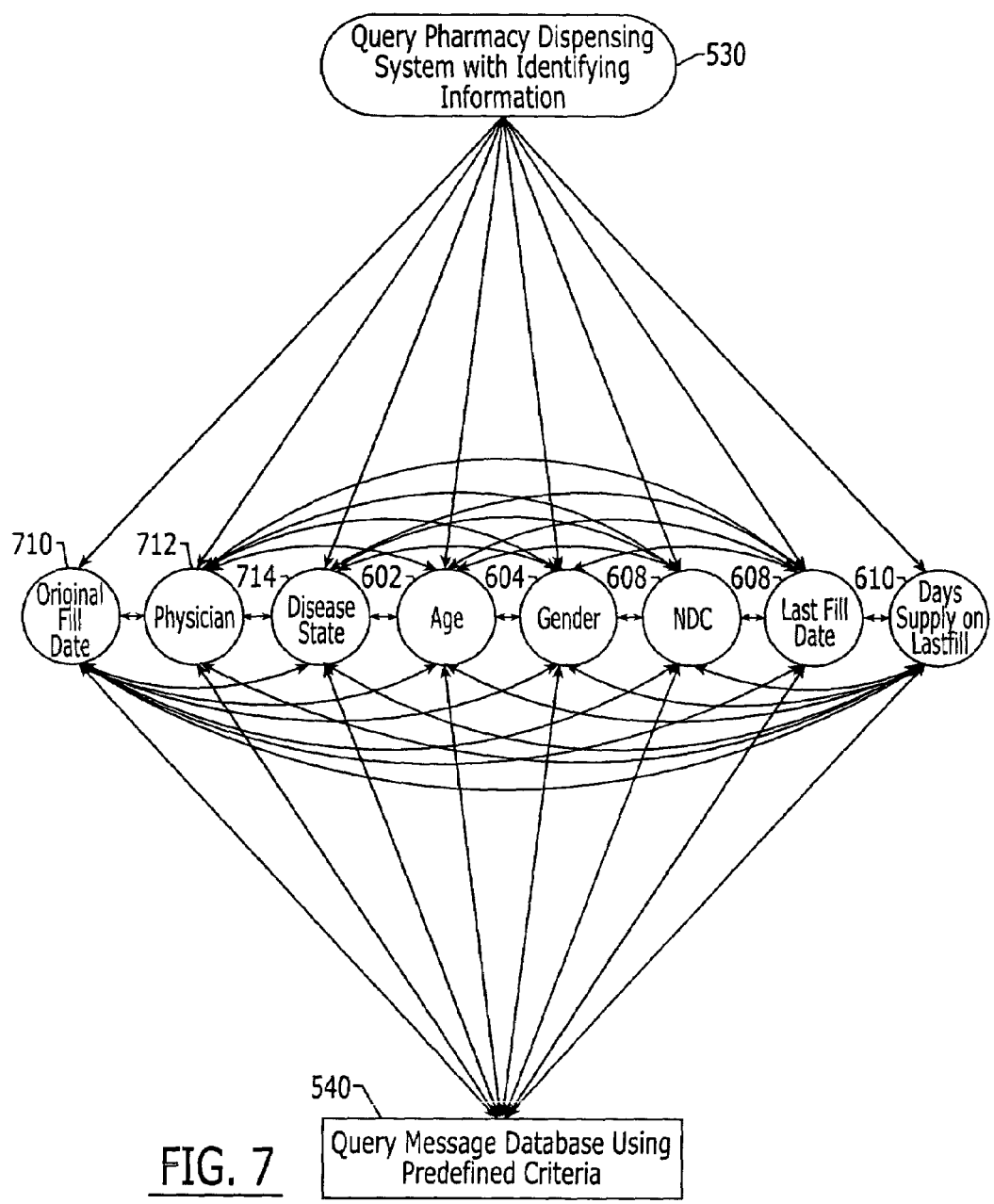

Returning again to FIG. 5, at Block 540, many types of predefined criteria may be used to query at least one database based on the identification of a pharmaceutical prescription, to thereby identify a targeted message. In some embodiments, combinations and subcombinations of five criteria may be queried. In particular, as shown in FIG. 6, age 602, gender 604, NDC (medication) 606, last fill date 608 and/or days supply on last fill 610 may be queried in order to query at least one database using predefined criteria at Block 540. FIG. 7 illustrates eight criteria including combinations and subcombinations of original fill date 710, physician 712 and disease state 714, in addition to criteria 602-610 of FIG. 6, which may be used to query at least one database using the predefined criteria at Block 540. Other combinations and subcombinations of these and/or other criteria may be used.

FIGS. 8-11 provide examples of targeted messages that may be generated based on querying at least one database using predefined criteria based on the identification of a pharmaceutical prescription to identify a targeted message, according to some embodiments of the present invention. These examples are illustrative and shall not be construed as limiting. Operations of these Figures may correspond to Blocks 530-560 of FIG. 5 and/or Blocks 230-250 of FIGS. 2 and 3. In particular, FIG. 8 will describe educational messages concerning the pharmaceutical prescription, FIGS. 9A and 9B will describe targeted messages that indicate alternative medications that may be substituted for the pharmaceutical prescription ("switching"), FIG. 10 will describe a targeted message that identifies other (related and/or unrelated) items that may be desired ("upselling") and FIG. 11 will describe a targeted message that solicits participation in a study related to the pharmaceutical prescription ("research/survey").

Figure 8:
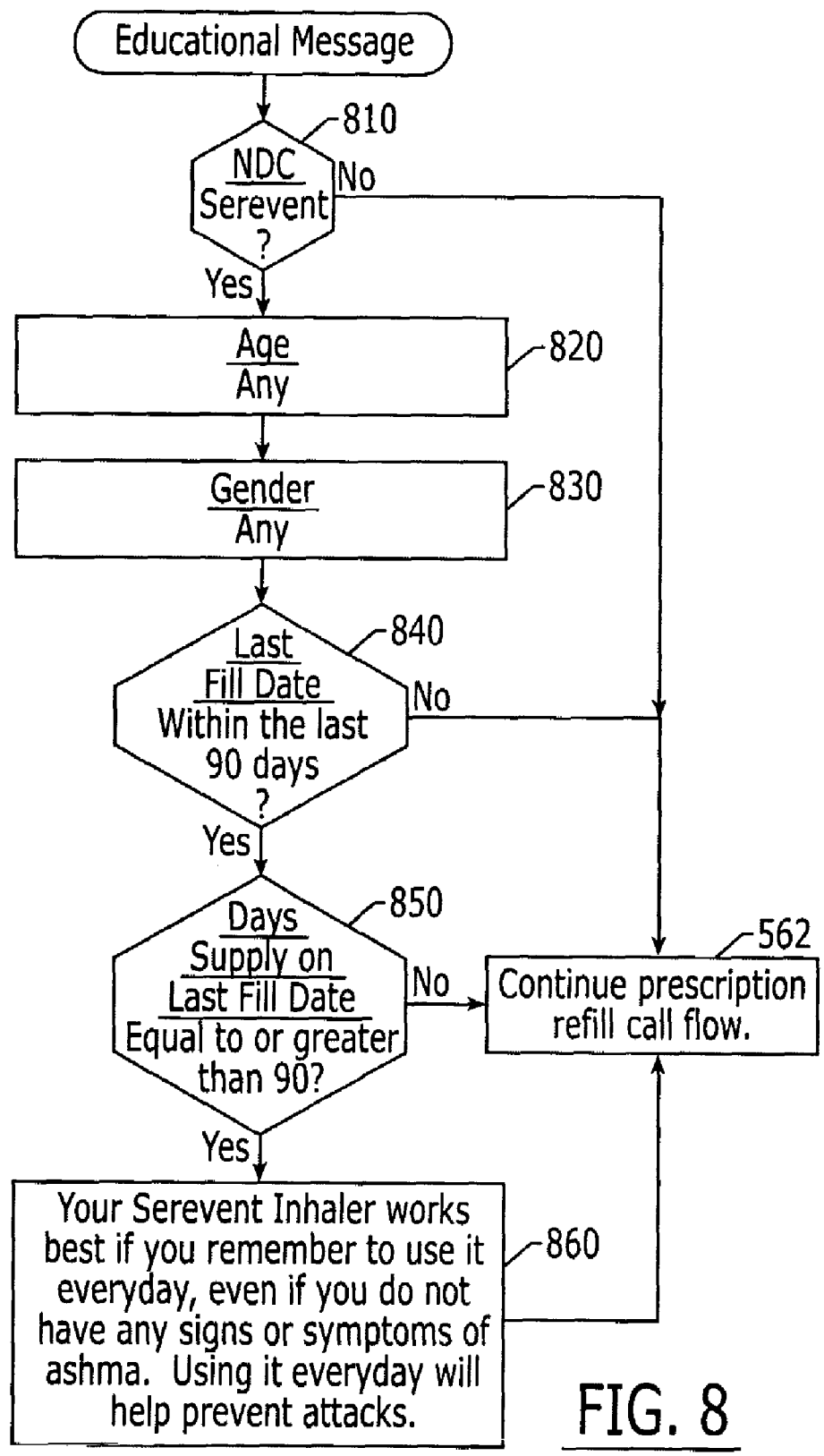
FIGS. 8-11 are flowcharts that illustrate examples of operations that may be performed to provide targeted messages according to various embodiments of the present invention.

Referring to FIG. 8, operations that may be performed to provide an educational message concerning the pharmaceutical prescription, according to some embodiments of the present invention, now will be described. As shown in FIG. 8, the following queries may be made to identify a targeted message matching the predefined criteria: At Block 810, a test is made as to whether the NDC (medication) corresponds to Serevent. If yes, at Block 820, any age, and at Block 830, any gender, may satisfy the criteria. At Block 840, a test is made as to whether the last fill date is within the last 90 days (or another first threshold) and at Block 850, a test is made as to whether the days supply on the last fill date is equal to or greater than 90 (or another second threshold which may or may not equal the first threshold).

If the tests of Blocks 810, 840 or 850 fail, then the prescription refill call flow is continued at Block 562, including testing relative to other sets of predetermined criteria. However, if these tests pass, then a targeted message is played at Block 860 to state, "Your Serevent inhaler works best if you remember to use it every day, even if you do not have any signs or symptoms of asthma. Using it every day will help prevent attacks." Thus, in FIG. 8, if a sufficient number of days of supply of the medication remain, the user is reminded to take the medication every day. An educational message is thereby provided. Accordingly, FIG. 8 illustrates embodiments of the present invention wherein at least one database is queried using a predefined criteria of last fill date and days supply on last fill date, based on the identification of a pharmaceutical prescription and identifying an educational target message that reminds the patient how to use the pharmaceutical prescription if the last fill date is less than a first threshold and the days supply on last fill date exceeds a second threshold which may or may not equal the first threshold. It also will be understood that in other embodiments, other predefined criteria may be used to provide an educational targeted message related to the pharmaceutical prescription.

Figure 9A:
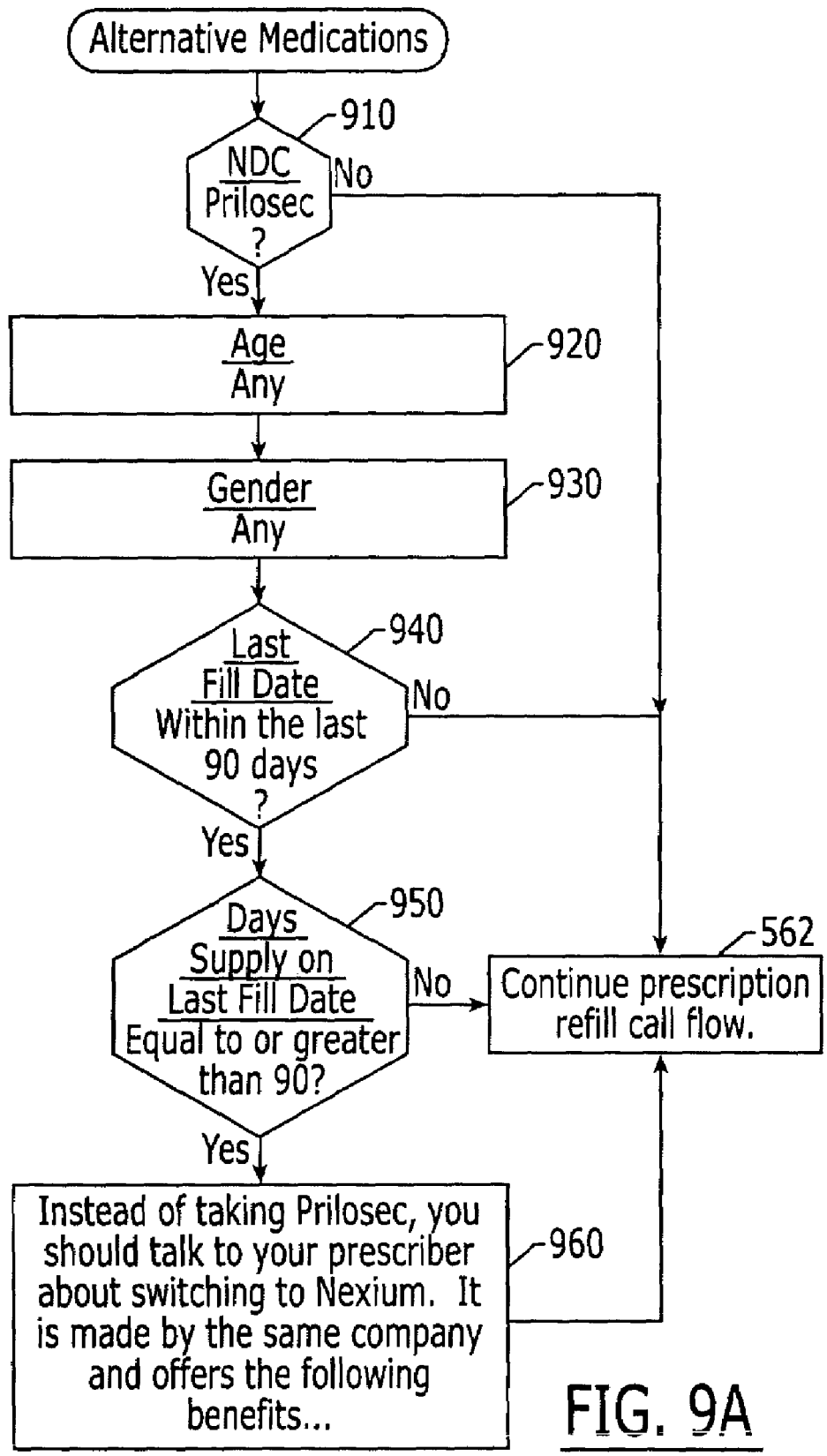
Figure 9B:
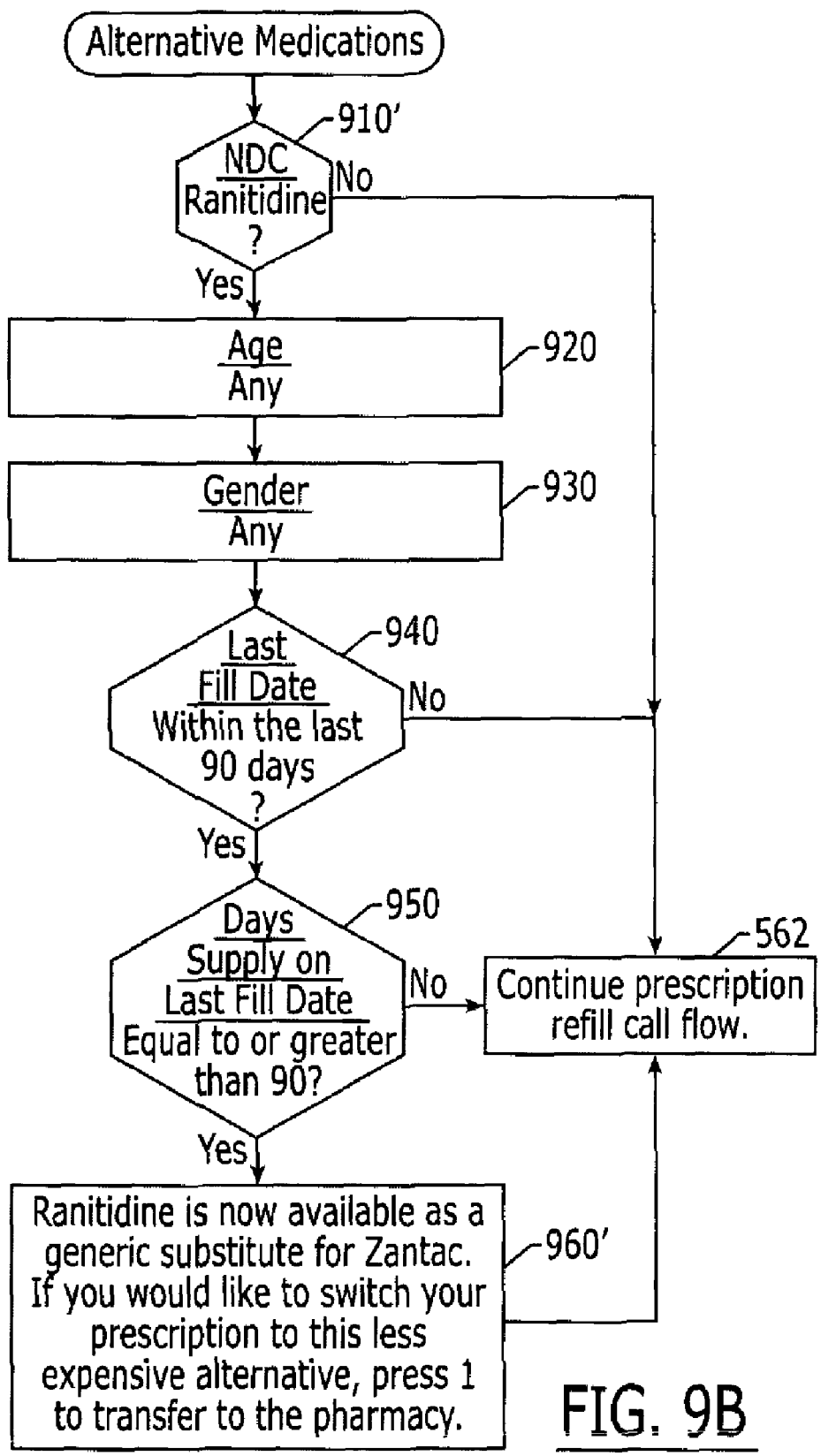

FIGS. 9A and 9B illustrate embodiments of the present invention, which can provide targeted messages that indicate alternative medications that may be substituted for the pharmaceutical prescription, i.e., a targeted message that can advise on switching to a different drug. In particular, referring to FIG. 9A, at Block 910, a test is made as to whether the NDC is Prilosec. At Block 920, any age may be identified and, at Block 930, any gender may be identified. At Block 940, if the last fill date is within the last 90 days and, at Block 950, if the days supply on the last fill date is equal to or greater than 90 days, then at Block 960, a message may be provided that states, "Instead of taking Prilosec, you should talk to your prescriber about switching to Nexium. It is made by the same company and offers the following benefits. . . ." Alternatively, if the tests of Blocks 910, 940 and 950 are not satisfied, then the prescription refill call flow may be continued at Block 562.

FIG. 9B illustrates similar operations for the drug Ranitidine at Block 910'. At Block 960', a message may be provided that, "Ranitidine is now available as a generic substitute for Zantac. If you would like to switch your prescription to this less expensive alternative, press 1 to transfer to the pharmacy." Accordingly, FIGS. 9A and 9B illustrates querying at least the database using predefined criteria of a last fill date and days supply on last fill date based on the identification of a pharmaceutical prescription, and identifying a targeted message that indicates alternative medications that may be substituted for the pharmaceutical prescription if the last fill date is less than a first threshold and the days supply on last fill date exceeds a second threshold, which may or may not be equal to the first threshold. It also will be understood that other predetermined criteria may be used to provide switching targeted messages, in other embodiments.

Figure 10:
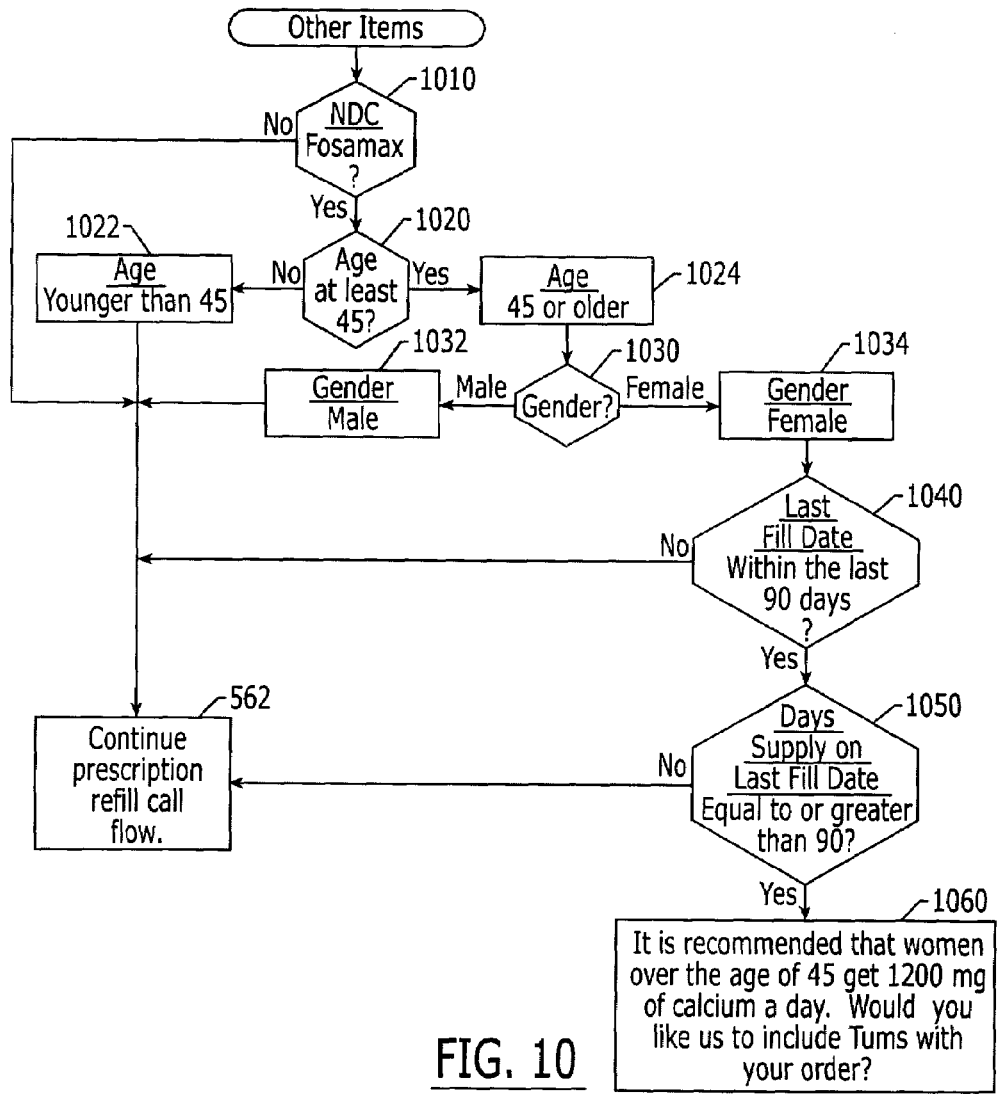

FIG. 10 is a flowchart of operations that may be performed to provide targeted messages regarding other items, also referred to as upselling, according to some embodiments of the present invention. The other items may include over-the-counter medications, supplies and/or other retail sales and add-on purchases, which may be related and/or unrelated to the prescribed product. At Block 1010, if the NDC (medication) is Fosomax, a test is made at Block 1020 as to whether age is at least 45. If the NDC is not Fosamax at Block 1010, or age is younger than 45 at Block 1022, then the prescription refill call flow may be continued at Block 562. However, if age is at least 45 at Block 1024, then at Block 1030, a test is made as to gender. If gender is male at Block 1032, then the prescription refill call flow may be continued at Block 562. However, if gender is female at Block 1034, then a test is made at Block 1040 as to whether the last fill date is within the last 90 days, and at Block 1050, as to whether the days supply on the last fill date is equal to or greater than 90 days. If these tests are passed, then at Block 1060, a targeted message is provided stating, "It is recommended that women over the age of 45 get 1200 mg of calcium a day. Would you like us to include Tums with your order?". Accordingly, FIG. 10 illustrates embodiments of the present invention wherein if the gender is female, the age exceeds a first threshold, last fill date is less than a second threshold (which may or may not equal the first threshold) and days supply on the last fill date exceeds a third threshold (which may or may not equal the first and/or second thresholds), a targeted message is identified that indicates other items that may be desired. These embodiments can include a query of NDC, age, gender, last fill date and days supply on last fill date. It also will be understood that other predetermined criteria may be used to provide upselling targeted messages in other embodiments.

Figure 11:
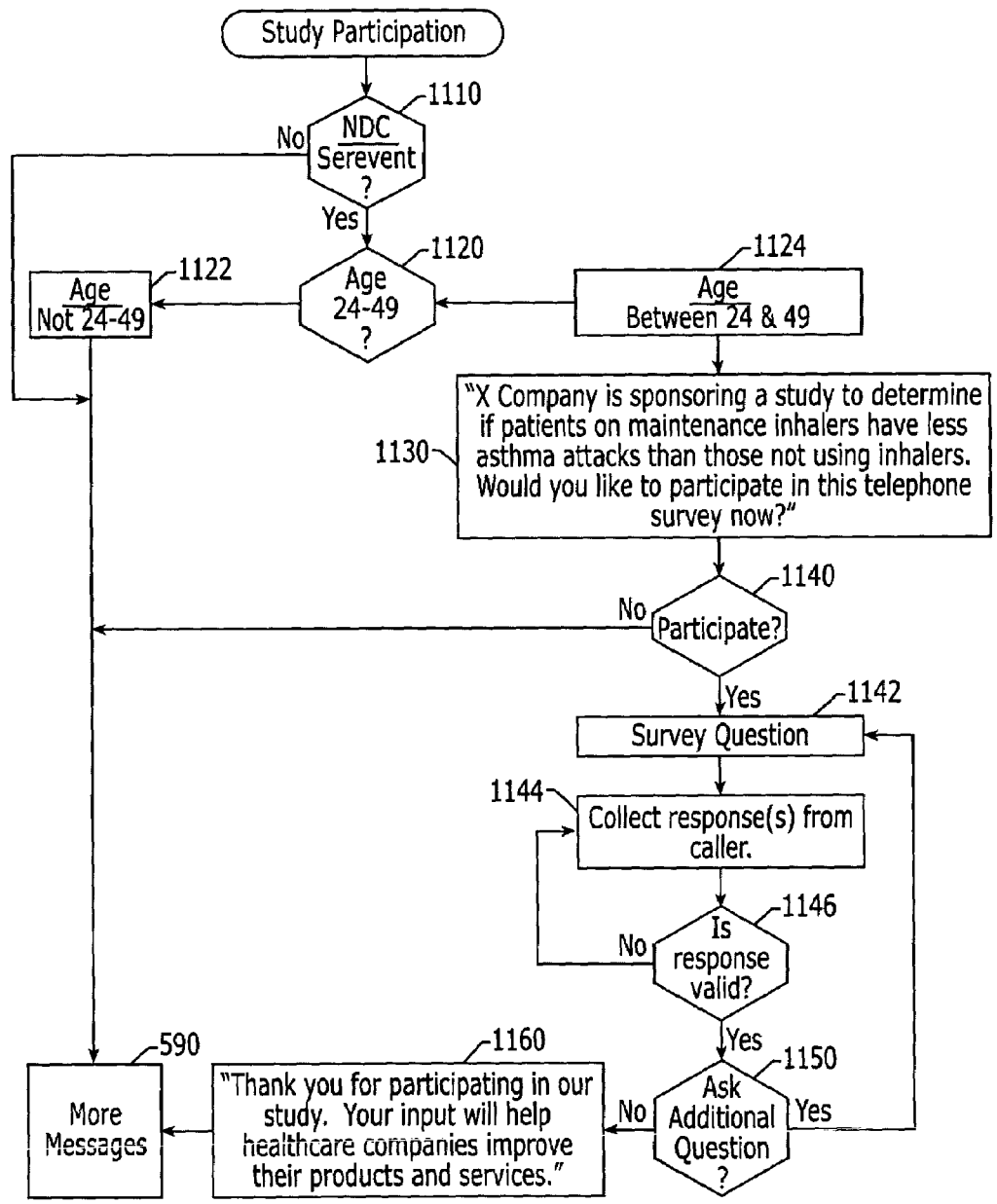

FIG. 11 is a flowchart of other embodiments of the present invention that may be used to provide a targeted message that solicits participation in a study related to the pharmaceutical prescription and/or allows the patient to actually participate in the study. It will be understood that, as used herein, a study can be a clinical trial, a survey and/or other study that is conventionally used in the pharmaceutical industry.

Referring now to FIG. 11, at Block 1110, a test is made as to whether the medication is identified as Serevent. At Block 1120, a test is made as to whether the age is between 24 and 49. If the tests at Blocks 1110 or 1120 fail, the prescription call flow may continue at Block 590. On the other hand, if at Block 1124 the age is between 24 and 49, then a targeted message may be played, at Block 1130, that indicates that a company is sponsoring a study and asking if the patient would like to participate in a telephone survey. At Block 1140, if the caller indicates that the patient wishes to participate, then at Block 1142, a survey question is asked. It will be understood by those having skill in the art that the question at Block 1140 may be asked to satisfy compliance rules for participation in the survey.

Continuing with the description of FIG. 11, at Block 1144, one or more responses are collected from the caller and tested for validity, at Block 1146. At Block 1150, if there are additional questions to ask, then the operations of Blocks 1142, 1144 and 1146 are repeatedly performed until there are no additional questions to ask. Once there are no additional questions to ask at Block 1150, a message may be sent at Block 1160 that thanks the caller for participating in the study. Accordingly, operations of FIG. 11 may be used to determine whether the age and/or gender qualifies the patient to participate in a study related to the pharmaceutical prescription and to identify a target message that solicits participation of the patient in the study related to the pharmaceutical prescription if the age and/or gender of the patient qualifies the caller to participate. Additional operations may be performed to provide messages to the caller, to complete the study related to the pharmaceutical prescription. It also will be understood that other predetermined criteria may be used to solicit study participation in other embodiments.

In the drawings and specification, there have been disclosed embodiments of the invention and, although specific terms are employed, they are used in a generic and descriptive sense only and not for purposes of limitation, the scope of the invention being set forth in the following claims.

What is claimed is:

1. A system for operating a pharmacy Interactive Voice Response (IVR) system comprising:
   at least one database; and
   a module that is configured to query the at least one database using predefined criteria based on an identification of a pharmaceutical prescription from a telephone caller to the pharmacy IVR system, to identify a targeted message based on the predefined criteria and to provide the targeted message to the pharmacy IVR system for playing to the caller
   wherein the predefined criteria based on the identification of a pharmaceutical prescription comprise age of a patient who is using the pharmaceutical prescription, gender of the patient, medication of the pharmaceutical prescription, last fill date of the pharmaceutical prescription, days supply on last fill of the pharmaceutical prescription, original fill date of the pharmaceutical prescription, disease state of the patient, physician of the patient and/or other promotions in effect.

2. A system according to claim 1 wherein the pharmacy (IVR) system is configured to answer a telephone call from a caller, accept identification of the pharmaceutical prescription from the caller and play the targeted message to the caller.

3. A system according to claim 2 wherein the pharmacy IVR system is further configured to execute a refill call flow for the pharmaceutical prescription.

4. A system according to claim 1 wherein the module is configured to query the at least one database using the predefined criteria based on the identification of a pharmaceutical prescription to identify a series of targeted messages and to provide a succeeding one of the series of targeted messages to the pharmacy IVR system in response to receipt of a caller response to a preceding one of the series of targeted messages from the pharmacy IVR system.

5. A system according to claim 1 wherein the pharmacy IVR system is further configured to receive a caller response to the targeted message.

6. A system according to claim 5 wherein the pharmacy IVR system is further configured to log the caller response.

7. A system according to claim 5 wherein the module is further configured to instruct the pharmacy IVR system to perform an action in response to the caller response to the targeted message.

8. A system according to claim 1 wherein the predefined criteria based on the identification of a pharmaceutical prescription do not include a personal identification of a patient who is using the pharmaceutical prescription.

9. A system according to claim 1 wherein the predefined criteria based on the identification of a pharmaceutical prescription do not include a personal identification of a patient who is using the pharmaceutical prescription.

10. A system according to claim 1 wherein the targeted message comprises an educational message concerning the pharmaceutical prescription, a message that indicates alternative medications that may be substituted for the pharmaceutical prescription, a message that identifies other items that may be desired by the patient and/or a message that solicits participation in a study related to the pharmaceutical prescription.

11. A system according to claim 1 wherein the module is configured to query by querying at least one database using the predefined criteria based on the identification of the pharmaceutical prescription to identify an educational targeted message related to the pharmaceutical prescription.

12. A system according to claim 1 wherein the at least one database comprises at least one pharmacy dispensing system database and at least one message database, and wherein the module is further configured to query by performing the following:
   querying the at least one pharmacy dispensing system database using the identification of the pharmaceutical prescription to identify the predetermined criteria; and
   querying the at least one message database using the predetermined criteria to identify a targeted message.

13. A system according to claim 1 wherein the identification of a pharmaceutical prescription is an Rx number.

14. A system for operating a pharmacy Interactive Voice Response (IVR) system comprising:
   at least one database; and
   a module that is configured to query the at least one database using predefined criteria based on an identification of a pharmaceutical prescription from a telephone caller to the pharmacy IVR system, to identify a targeted message based on the predefined criteria and to provide the targeted message to the pharmacy IVR system for playing to the caller, wherein the module is further configured to query by performing the following:

querying the at least one database using age of a patient who is using the pharmaceutical prescription, gender of the patient, medication of the pharmaceutical prescription, last fill date of the pharmaceutical prescription, days supply on last fill of the pharmaceutical prescription, original fill date of the pharmaceutical prescription, disease state of the patient, physician of the patient and/or other promotions in effect, based on the identification of a pharmaceutical prescription; and identifying a targeted message that corresponds to the age of the patient, gender of the patient, medication of the pharmaceutical prescription, last fill date of the pharmaceutical prescription, days supply on last fill of the pharmaceutical prescription, original fill date of the pharmaceutical prescription, disease state of the patient, physician of the patient and/or other promotions in effect.

15. A system according to claim 14 wherein the targeted message comprises a message that solicits participation in a study related to the pharmaceutical prescription.

16. A system according to claim 15 wherein the module is further configured to provide additional targeted messages to allow the patient to participate in the study if the patient agrees to participate.

17. A system according to claim 14 wherein the targeted message comprises a study question.

18. A system according to claim 17 wherein the module is further configured to receive a caller response to the targeted message comprising a study question.

19. A system according to claim 18 wherein the module is further configured to log the caller response to the targeted message comprising a study question.

20. A system for operating a pharmacy Interactive Voice Response (IVR) system comprising:
at least one database; and
a module that is configured to query the at least one database using predefined criteria based on an identification of a pharmaceutical prescription from a telephone caller to the pharmacy IVR system, to identify a targeted message based on the predefined criteria and to provide the targeted message to the pharmacy IVR system for playing to the caller
wherein the module is configured to query by performing the following:
querying at least one database using predefined criteria of last fill date and days supply on last fill date based on the identification of a pharmaceutical prescription; and
identifying an educational targeted message that reminds the caller how to use the pharmaceutical prescription if the last fill date is less than a first threshold and the days supply on last fill date is greater than a second threshold.

21. A system for operating a pharmacy Interactive Voice Response (IVR) system comprising:
at least one database; and
a module that is configured to query the at least one database using predefined criteria based on an identification of a pharmaceutical prescription from a telephone caller to the pharmacy IVR system, to identify a targeted message based on the predefined criteria and to provide the targeted message to the pharmacy IVR system for playing to the caller
wherein the module is configured to query by performing the following:
querying at least one database using predefined criteria of last fill date and days supply on last fill date based on the identification of a pharmaceutical prescription; and
identifying a targeted message that indicates alternative medications that may be substituted for the pharmaceutical prescription if the last fill date is less than a first threshold and the days supply on last fill date exceeds a second threshold.

22. A system for operating a pharmacy Interactive Voice Response (IVR) system comprising:
at least one database; and
a module that is configured to query the at least one database using predefined criteria based on an identification of a pharmaceutical prescription from a telephone caller to the pharmacy IVR system, to identify a targeted message based on the predefined criteria and to provide the targeted message to the pharmacy IVR system for playing to the caller
wherein the module is configured to query by performing the following:
querying at least one database using predefined criteria of age, gender, last fill date and days supply on last fill date based on the identification of a pharmaceutical prescription; and
identifying a targeted message that indicates other items that may be desired if the gender is female, the age exceeds a first threshold, last fill date is less than a second threshold and days supply on last fill date exceed a third threshold.

23. A system for operating a pharmacy Interactive Voice Response (IVR) system comprising:
at least one database; and
a module that is configured to query the at least one database using predefined criteria based on an identification of a pharmaceutical prescription from a telephone caller to the pharmacy IVR system, to identify a targeted message based on the predefined criteria and to provide the targeted message to the pharmacy IVR system for playing to the caller
wherein the module is configured to query by performing the following:
querying at least one database using a predefined criterion of age of a patient who is using the pharmaceutical prescription based on the identification of a pharmaceutical prescription; and
identifying a targeted message that solicits participation of the patient in a study related to the pharmaceutical prescription if the age of the patent qualifies the patient to participate in the study related to the pharmaceutical prescription.

24. A system according to claim 23 wherein the module is further configured to provide additional targeted messages to allow the patient to participate in the study if the patient agrees to participate.

25. A pharmacy Interactive Voice Response (IVR) system comprising:
means for answering a telephone call from a caller;
means for accepting identification of a pharmaceutical prescription from the caller;
means for querying at least one database using predefined criteria based on the identification of a pharmaceutical prescription to identify a targeted message; and
means for playing the targeted message to the caller
wherein the predefined criteria based on the identification of a pharmaceutical prescription comprise age of a patient who is using the pharmaceutical prescription, gender of the patient, medication of the pharmaceutical prescription, last fill date of the pharmaceutical prescription, days supply on last fill of the pharmaceutical prescription, original fill date of the pharmaceutical prescription, disease state of the patient, physician of the patient and/or other promotions in effect.

26. A system according to claim 25
wherein the means for querying comprises means for querying at least one database using the predefined criteria based on the identification of a pharmaceutical prescription to identify a series of targeted messages; and
wherein the means for playing comprises means for playing a succeeding one of the series of targeted messages to the caller in response to receipt of a caller response to a preceding one of the series of targeted messages.

27. A system according to claim 25 wherein the predefined criteria based on the identification of a pharmaceutical prescription do not include a personal identification of a patient who is using the pharmaceutical prescription.

28. A system according to claim 25 wherein the predefined criteria based on the identification of a pharmaceutical prescription do not include a personal identification of a patient who is using the pharmaceutical prescription.

29. A system according to claim 25 wherein the targeted message comprises an educational message concerning the pharmaceutical prescription, a message that indicates alternative medications that may be substituted for the pharmaceutical prescription, a message that identifies other items that may be desired and/or a message that solicits participation in a study related to the pharmaceutical prescription.

30. A system according to claim 25 wherein the means for querying comprises means for querying at least one database using the predefined criteria based on the identification of the pharmaceutical prescription to identify an educational targeted message related to the pharmaceutical prescription.

31. A system according to claim 25 wherein the means for querying comprises:
means for querying at least one database using a predefined criterion of age of a patient who is using the pharmaceutical prescription based on the identification of a pharmaceutical prescription; and
means for identifying a targeted message that solicits participation of the caller in a study related to the pharmaceutical prescription if the age of the patient qualifies the patient to participate in the study related to the pharmaceutical prescription.

32. A system according to claim 25 wherein the means for querying comprises:
means for querying at least one pharmacy dispensing system database using the identification of the pharmaceutical prescription to identify the predetermined criteria; and
means for querying at least one message database using the predetermined criteria to identify a targeted message.

33. A pharmacy Interactive Voice Response (IVR) system comprising:
means for answering a telephone call from a caller;
means for accepting identification of a pharmaceutical prescription from the caller;
means for querying at least one database using predefined criteria based on the identification of a pharmaceutical prescription to identify a targeted message; and
means for playing the targeted message to the caller, wherein the means for querying comprises:
means for querying at least one database using age of a patient who is using the pharmaceutical prescription, gender of the patient, medication of the pharmaceutical prescription, last fill date of the pharmaceutical prescription, days supply on last fill of the pharmaceutical prescription, original fill date of the pharmaceutical prescription, disease state of the patient, physician of the patient and/or other promotions in effect, based on the identification of a pharmaceutical prescription; and
means for identifying a targeted message that corresponds to the age of the patient, gender of the patient, medication of the pharmaceutical prescription, last fill date of the pharmaceutical prescription, days supply on last fill of the pharmaceutical prescription, original fill date of the pharmaceutical prescription, disease state of the patient, physician of the patient and/or other promotions in effect.

34. A system according to claim 33 wherein the targeted message comprises a message that solicits participation in a study related to the pharmaceutical prescription.

35. A system according to claim 34 further comprising:
means for providing additional targeted messages to allow the patient to participate in the study if the patient agrees to participate.

36. A system according to claim 33 wherein the targeted message comprises a study question.

37. A system according to claim 36 further comprising:
means for receiving a caller response to the targeted message comprising a study question.

38. A system according to claim 37 further comprising:
means for logging the caller response to the targeted message comprising a study question.

39. A pharmacy Interactive Voice Response (IVR) system comprising:
means for answering a telephone call from a caller;
means for accepting identification of a pharmaceutical prescription from the caller;
means for querying at least one database using predefined criteria based on the identification of a pharmaceutical prescription to identify a targeted message; and
means for playing the targeted message to the caller
wherein the means for querying comprises:
means for querying at least one database using predefined criteria of last fill date and days supply on last fill date based on the identification of a pharmaceutical prescription; and
means for identifying an educational targeted message that reminds the caller how to use the pharmaceutical prescription if the last fill date is less than a first threshold and the days supply on last fill date is greater than a second threshold.

40. A pharmacy Interactive Voice Response (IVR) system comprising:
means for answering a telephone call from a caller;
means for accepting identification of a pharmaceutical prescription from the caller;
means for querying at least one database using predefined criteria based on the identification of a pharmaceutical prescription to identify a targeted message; and
means for playing the targeted message to the caller
wherein the means for querying comprises:
means for querying at least one database using predefined criteria of last fill date and days supply on last fill date based on the identification of a pharmaceutical prescription; and
means for identifying a targeted message that indicates alternative medications that may be substituted for the pharmaceutical prescription if the last fill date is less than a first threshold and the days supply on last fill date exceeds a second threshold.

41. A pharmacy Interactive Voice Response (IVR) system comprising:
  means for answering a telephone call from a caller;
  means for accepting identification of a pharmaceutical prescription from the caller;
  means for querying at least one database using predefined criteria based on the identification of a pharmaceutical prescription to identify a targeted message; and
  means for playing the targeted message to the caller wherein the means for querying comprises:
  means for querying at least one database using predefined criteria of age, gender, last fill date and days supply on last fill date based on the identification of a pharmaceutical prescription; and
  means for identifying a targeted message that indicates other items that may be desired if the gender is female, the age exceeds a first threshold, last fill date is less than a second threshold and days supply on last fill date exceed a third threshold.

* * * * *